US00PP21820P2

(12) United States Plant Patent
Rogalski

(10) Patent No.: US PP21,820 P2
(45) Date of Patent: Mar. 29, 2011

(54) ***DAPHNE* PLANT NAMED 'ROGBRET'**
(50) Latin Name: *Daphne odora*
Varietal Denomination: Rogbret

(76) Inventor: Przemyslaw Rogalski, Saint Gilles les Bois (FR)

( * ) Notice: Subject to any disclaimer, the term of this patent is extended or adjusted under 35 U.S.C. 154(b) by 0 days.

(21) Appl. No.: 12/583,523

(22) Filed: Aug. 22, 2009

(51) Int. Cl.
*A01H 5/00* (2006.01)

(52) U.S. Cl. ..... Plt./226

(58) Field of Classification Search ..... Plt./226

See application file for complete search history.

*Primary Examiner*—Susan B McCormick Ewoldt

(57) ABSTRACT

A new and distinct *Daphne* cultivar named 'Rogbret' is disclosed, characterized by variegated leaves with a distinctive large yellow band on margin, resistance to deciduousness in winter months, making the new cultivar a true evergreen and an open, spreading plant habit. The new cultivar is a *Daphne*, suitable for ornamental garden purposes.

2 Drawing Sheets

Latin name of the genus and species: *Daphne odora.*
Variety denomination: 'ROGBRET'.

BACKGROUND OF THE INVENTION

The new cultivar is a product of a chance discovery in a commercial setting by the inventor. In 2004, the inventor, Przemyslaw Rogalski discovered an interesting single branch mutation in a commercial planting of the unpatented parent variety *Daphne odora* 'Aureomarginata'. This single branch mutation was discovered at a commercial nursery in Saint Gilles Les Bois, France.

During 2004 the inventor propagated the interesting mutation by semi-hardwood cuttings at the commercial nursery in Saint Gilles Les Bois in France. The initial propagation showed the mutation to be stable and additional generations were propagated, also by semi-hardwood cuttings. Approximately 6 generations have been reproduced since 2004, and have shown that the unique features of this cultivar are stable and reproduced true to type.

SUMMARY OF THE INVENTION

The cultivar 'Rogbret' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'Rogbret' These characteristics in combination distinguish 'Rogbret' as a new and distinct *Daphne* cultivar:

1. Variegated leaves with a distinctive large yellow band on margin.
2. Resistance to deciduousness in winter months, making the new cultivar a true evergreen.
3. Open, spreading plant habit.

COMPARISON TO PARENT VARIETY

Plants of the new cultivar 'Rogbret' are similar to plants of the parent; *Daphne odora* 'Aureomarginata' in most horticultural characteristics, however, plants of the new cultivar 'Rogbret' have foliage with a significantly more pronounced variegation, including a much wider yellow band on the margin. Additionally, foliage of 'Rogbret' is persistent in the winter, whereas 'Aureomarginata' is semi-deciduous. The older, woody branches of 'Rogbret' are softer than older, woody branches of 'Aureomarginata' of a similar age.

COMMERCIAL COMPARISON

'Rogbret' is best compared to the commercial variety *Daphne odora* 'Hewreb' U.S. Plant Pat. No. 18,368. Plants of the new cultivar 'Rogbret' are similar to plants of 'Hewreb' in most horticultural characteristics, however, plants of the new cultivar 'Rogbret' have a more spreading overall plant habit. Additionally, plants of 'Rogbret' are fully evergreen, whereas plant of 'Hewreb' are semi-deciduous in winter. Flower color of 'Rogbret' tends towards Red-Purple shades according to R.H.S. charts, whereas 'Hewreb' tends towards Purple shades.

BRIEF DESCRIPTION OF THE PHOTOGRAPH

The accompanying photograph in

Figure 1:
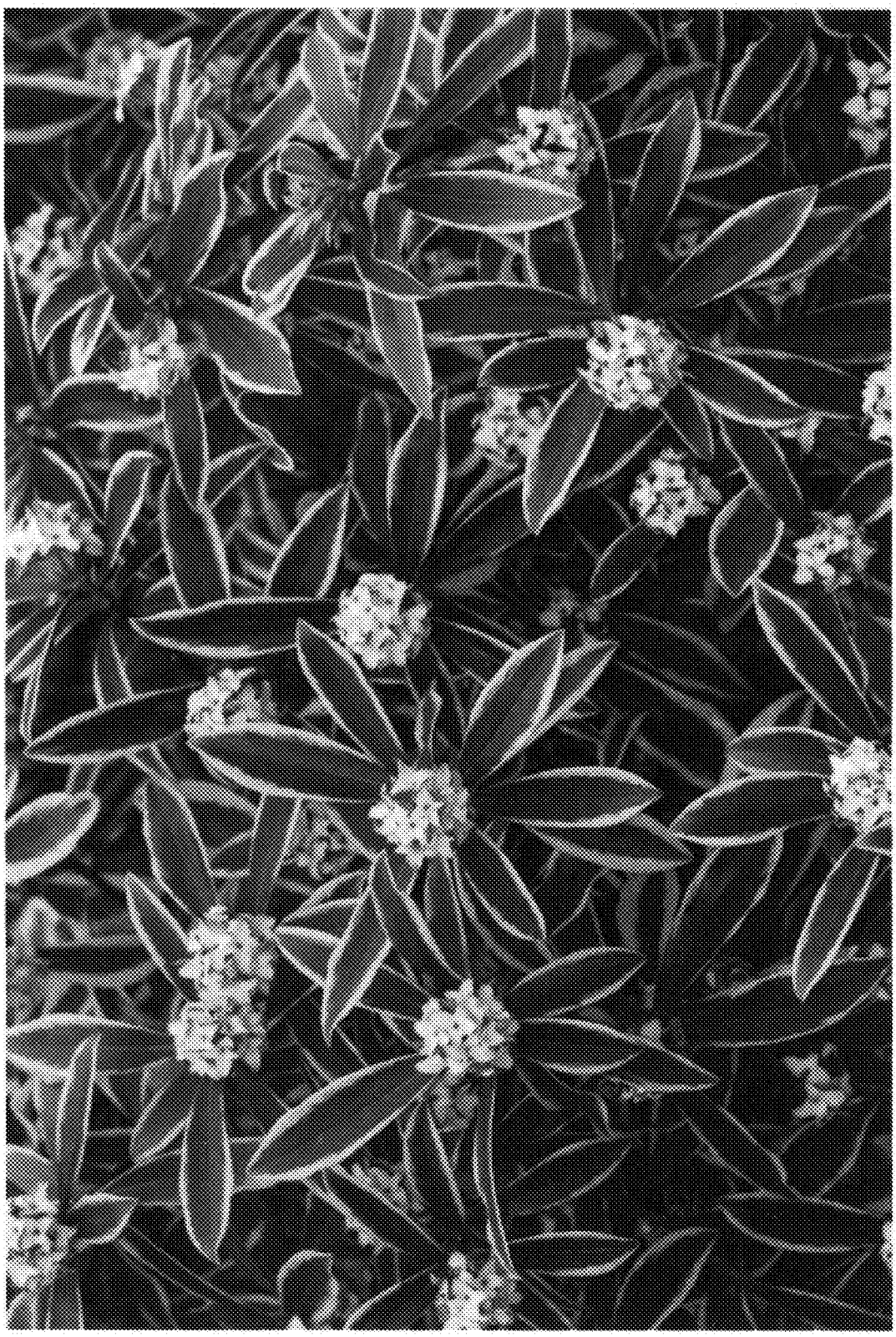
FIG. 1 illustrates in full color a close up of typical foliage and flowers of 'Rogbret' grown outdoors in France.
Figure 2:
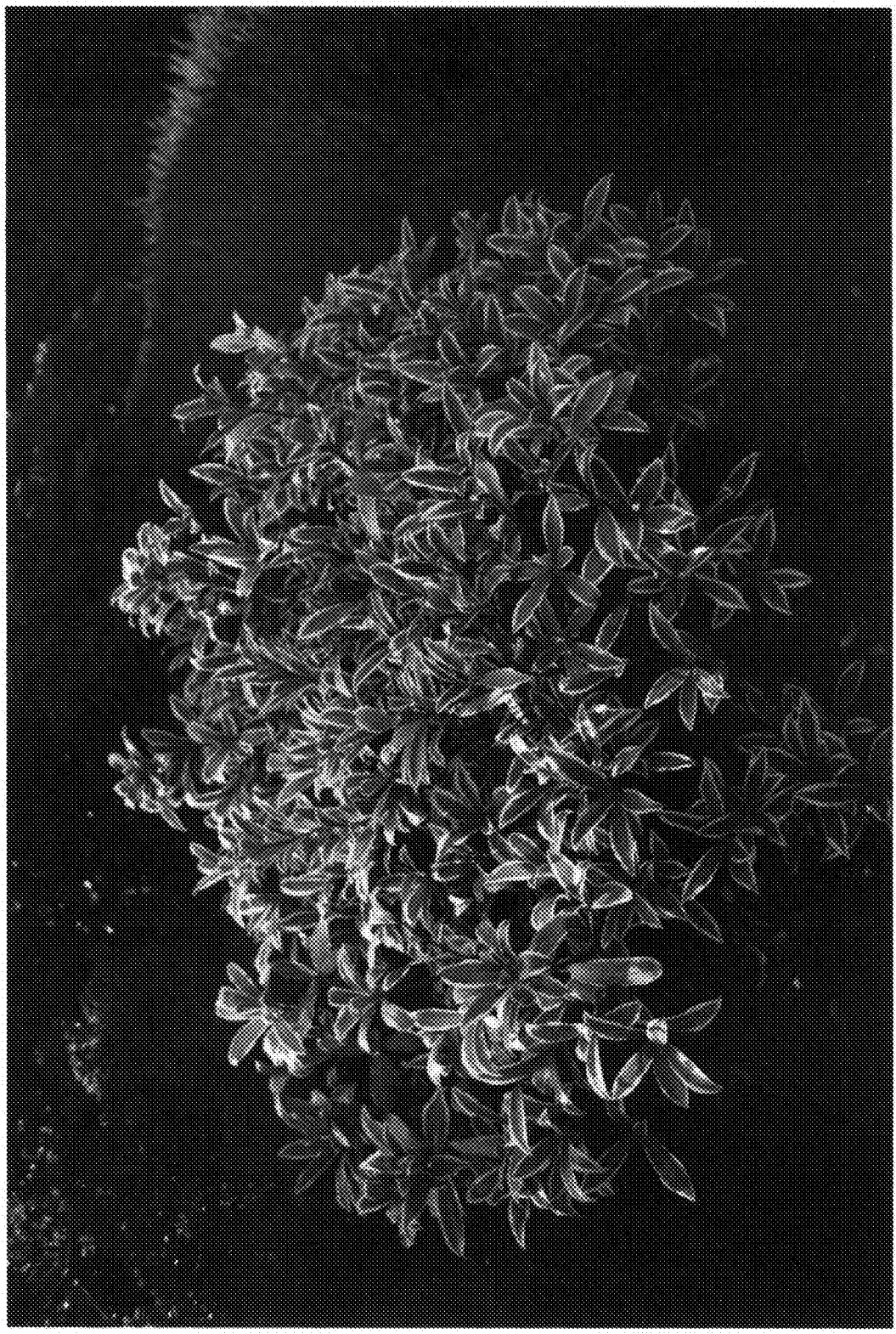
FIG. 2 illustrates in full color a typical plant of 'Rogbret' grown outdoors in France.

The plant is approximately 5 years old, and is planted in the ground. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'Rogbret' plants grown in a greenhouse in Saint Gilles Les Bois, France. Plants are approximately 3 years old, in a 3 liter nursery container. Additionally, for the purpose of describing older wood, 5 year old plants growing outdoors in Saint Gilles Les Bois, France were also used. All data is taken from the 3 year old greenhouse plants, unless specifically designated in the botanical description that the information is from the 5 year old plants. The greenhouse is unheated and unshaded. Temperatures ranged from 2° C. to 20° C. at night to 5° C. to 35° C. during the day. Measurements and numerical values represent averages of typical plant types.

Botanical classification: *Daphne odora* 'Rogbret'.

PROPAGATION

Time to rooting: Approximately 4 to 8 weeks at approximately 20° C. to 30° C. from semi-hardwood cuttings.

Root description: Fine, fibrous young roots. Older roots becoming woody.

PLANT

Growth habit: Upright and outwardly spreading shrub. Moderately dense.

Height: Outdoors, after approximately 5 years: Approximately 65 cm. Greenhouse, 3 liter pot, 3 years old, Approximately 40 cm.

Plant spread: Outdoors, after approximately 5 years: Approximately 100 cm. Greenhouse, 3 liter pot, 3 years old, Approximately 50 cm.

Growth rate: Approximately 10 to 15 cm per year.

Branching characteristics: Moderate to light branching, angled approximately 45 to 75 degrees.

Length of lateral branches: Approximately 12 to 20 cm.

Number of lateral branches: Approximately 3 main lateral branches on a 3 year old plant.

Diameter of lateral branches: Approximately 0.35 to 0.5 cm.

Lateral branch strength: Very strong, with some flexibility.

Lateral branch color: Young branches near RHS Yellow-Green 144B. Mature branches (more than 3 years) near RHS Brown 200D.

Other stem or plant characteristics: No pubescence or lenticels observed. Texture moderately rough.

Number of leaves per lateral branch: Average 10 to 15.

Age of plant described: Approximately 3 years.

FOLIAGE

Leaf:

*Type.*—Simple.

*Arrangement.*—Alternate.

*Average length.*—Approximately 6 to 10 cm.

*Average width.*—Approximately 1.6 to 2.4 cm.

*Shape of blade.*—Elliptic to obovate.

*Apex.*—Mucronate.

*Base.*—Cuneate.

*Attachment.*—Sessile.

*Margin.*—Entire.

*Texture of top surface.*—Smooth.

*Texture of bottom surface.*—Smooth.

*Leaf internode length.*—Approximately 0.9 to 1.5 cm.

*Color.*—Young foliage upper side: Center near RHS Green 137A. Margin can be RHS Yellow 10A or 10B or 10C. Margin is approximately 0.3 cm wide. Young foliage under side: Center near RHS 147B. Margin can be RHS Yellow 11B or 11C. Margin is approximately 0.3 cm wide. Mature foliage upper side: Center near RHS Yellow-Green 146A. Margin near RHS Yellow 10A or 10B. Margin is approximately 0.3 to 0.5 cm wide. Mature foliage under side: Center near RHS 146C. Margin near RHS Yellow 11B or 11C. Margin is approximately 0.3 to 0.5 cm wide.

*Venation.*—Type: Pinnate. Venation color upper side: A range including colors Near RHS Yellow 10A through 10C. Venation color under side: Near RHS Yellow-Green 145C.

Petiole: Not present, sessile.

Bloom period:

*Natural season.*—December to March.

Inflorescence:

*Arrangement.*—Single trumpet shaped flowers, composed of petaloid sepals clustered in terminal heads. Corolla not present.

*Diameter.*—Approximately 3.5 cm.

*Depth.*—Approximately 3 cm.

*Quantity of flowers per inflorescence.*—Approximately 16 to 18.

Flower:

*Facing direction.*—Out and up.

*Diameter of entire flower.*—Approximately 1 cm.

*Depth/length of flower.*—Approximately 2 cm.

*Persistent or self-cleaning.*—Self-cleaning.

*Fragrance.*—Very strong *Daphne* scent.

Petaloid sepals:

*Length.*—Approximately 1.0 cm.

*Width.*—Approximately 0.5 cm.

*Apex.*—Acute.

*Shape of petal.*—Ovate.

*Petal margin.*—Entire, slightly rolled inward.

*Petal arrangement.*—Whorled.

*Petal number.*—4.

*Petal texture.*—Smooth.

*Color.*—Upper surface at first opening: Near RHS White N155B with margin flushed near RHS Red-Purple 63A. Upper surface at maturity: Near RHS White N155B with very slight margin flushed near RHS Red-Purple 63C. Upper surface at fading: Near RHS White N155B. Under surface at first opening: Near RHS Red-Purple 63B. Under surface at maturity: Near RHS Red-Purple 61A or B. Under surface at fading: Near RHS Red-Purple 62C.

OTHER CHARACTERISTICS

Disease and pest resistance: Not observed to be susceptible nor resistant to normal diseases and pests of *Daphne odora*.

Drought tolerance: Some drought tolerance. Plants will not wilt or suffer significant damage if regular supplemental waterings are missed.

Low temperature tolerance: Hardy in France to −20° C.

High temperature tolerance: High temperature tolerance is not exactly know. Tolerates at least 30° C.

Fruit/seed production: Not observed after 5 years.

What is claimed is:

1. A new and distinct cultivar of *Daphne* plant named 'Rogbret' as herein illustrated and described.

* * * * *